(12) United States Patent
Schmid et al.

(10) Patent No.: US 6,273,855 B1
(45) Date of Patent: Aug. 14, 2001

(54) METHOD AND DEVICE FOR COMPRESSED OPTICAL REPRESENTATION OF MEDICAL DATA

(75) Inventors: Guenter Schmid, Germering; Josef Herzner, Munich; Uwe Becker, Groebenzell, all of (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 09/312,391

(22) Filed: May 14, 1999

(30) Foreign Application Priority Data

May 14, 1998 (DE) .............................................. 198 21 761

(51) Int. Cl.$^7$ ....................................................... A61B 5/00
(52) U.S. Cl. ......................... 600/300; D24/107; 178/898
(58) Field of Search .................................... 600/300–301, 600/529–538; 128/920–925, 898, 897

(56) References Cited

U.S. PATENT DOCUMENTS

| 5,111,827 | 5/1992 | Rantala . | |
|---|---|---|---|
| 6,001,060 | * 12/1999 | Churchill et al. | 600/300 |
| 6,026,320 | * 2/2000 | Carlson et al. | 600/300 |

OTHER PUBLICATIONS

Visual Display Format Affects the Ability of Anesthesiologists to Detect Acute Physiologic Changes: in Anesthesiology, vol. 83, pp. 1184–1193.

"An Integrated Graphic Data Display Improves Detection and Idnetification of Critical Events During Anesthesia" In Journal of Clinical Monitoring, vol. 13, pp. 249–259.

"Beatmungs– und Narkosetechniken", A Gartner, TUV RheinTand.

"Beatmungsgerate in der Intensivmedizin" in Anaesthesist, vol. 42, S. 396–417.*

"Moderne Beatmungsformen" in Anaesthesist, vol. 42, S. 813–832.*

* cited by examiner

*Primary Examiner*—Eric F. Winakur
*Assistant Examiner*—Michael C Astorino
(74) *Attorney, Agent, or Firm*—Diller, Ramik & Wight

(57) ABSTRACT

The invention relates to a method for simultaneous compressed visual representation of the data of three or more medically relevant parameters, wherein the data of the parameters are represented in a coordinate system with three or more dimensions, this coordinate system together with the data of the parameters represented therein is transformed into a two-dimensional coordinate system through a preset arithmetic rule and the result of this transformation is displayed in the display area of a display device, with the essential features of the data of at least one of the parameters being periodic over time. The invention further relates to a monitoring device wherein the inventive method is realized.

16 Claims, 3 Drawing Sheets

METHOD AND DEVICE FOR COMPRESSED OPTICAL REPRESENTATION OF MEDICAL DATA

BACKGROUND OF THE INVENTION

The present invention relates to medical systems and particularly patient monitoring systems for the acquisition, processing and display of data of critically ill patients.

When monitoring critically ill patients, it is often necessary to obtain a variety of medical data related to the condition of the patient. Various options are available for this purpose. The most frequently chosen options are the use of patient monitoring devices for the acquisition of physiological parameters, such as those of the electrocardiogram, of the blood pressure, of the oxygen saturation or of the respiration; the laboratory analysis of physiological samples, e.g. of blood or tissue samples, and, in patients treated by artificial respiration, the evaluation of settings and measurement values of the respiration device. Recently, particularly the data acquired by a patient surveillance monitor have rapidly increased in number, on the one hand because the technical progress achieved in the fields of sensor technology and microelectronics is beneficial for the monitoring of patients, and on the other hand because the increasing insight into the medical interrelationships has initiated a demand for the acquisition of further parameters.

Due to this recent development, the number of a patient's physiological parameters which can be acquired, processed and displayed in modern intensive care wards and operating theaters has become so large that even very sophisticated display instruments make it hardly possible anymore to quickly acquire the massive bulk of data and that a reasonable evaluation of these data by the medical staff is hardly feasible either. Since humans can only visually observe a relatively limited number of curves and varying measurement values simultaneously and draw correct conclusions from these observations, state-of-the-art patient monitoring systems clearly entail a so-called "mental overload" effect, i.e. an overstrain of the mental receptivity. This makes it necessary to develop methods for avoiding the above effect.

The existence of a clear interrelationship between the form of representation of physiological data and the medical staff's ability to interpret these data has been demonstrated in a study published in Anesthesiology, Vol. 83, pp. 1184–1193 and entitled "Visual Display Format Affects the Ability of Anesthesiologists to Detect Acute Physiologic Changes". This study evaluates different forms of presentation of physiological data and the speed and accuracy of the detection of changes in these physiological data as performed by the medical staff. This study comes to the conclusion that the physiological data can be interpreted in a distinctly faster and more accurate manner when presented in a graphical form. A similar result has been presented in a study published in Journal of Clinical Monitoring, Vol. 13, pp. 249–259 and entitled "An Integrated Graphic Data Display Improves Detection and Identification of Critical Events During Anesthesia" wherein a graphic representation of twenty anesthesia-related parameters is compared to a mode of representation performed by means of curves and numerical values of the type commonly used in patient monitoring devices according to the state of the art. As to the detection of relevant events by the medical staff, the conventional representation through curves and numerical values has proven to require several minutes, additional time in comparison to a new graphic representation.

Since, as described above, the number of parameters monitored in a critically ill patient is ever more increasing, whereas the size of the monitoring devices is hardly changing or is even reduced as a result of technical advances, the display of the totality of such parameters on the screen of a monitoring device will cause a dilemma. Frequently, certain monitored parameters are displayed not at all or only with insufficient size and quality on the screen of a monitoring device because the space. available on the monitoring screen is not sufficient for displaying all of the monitored parameters with satisfactory quality. Other parameters, although their monitoring would be beneficial from the medical viewpoint, are not monitored since the display space of the monitoring device is already exhausted by other parameters of higher medical importance.

Thus, it is an object of the present invention to provide a method and a device for the optical representation of medical data acquired by medical systems, wherein the data can be quickly acquired and evaluated by a viewer.

SUMMARY OF THE INVENTION

The present invention avoids the disadvantages of the display of medical data inherent to medical systems of the prior art in that the space requirements for the display of these medical data are considerably reduced. Further, the visual displays generated by the method according to the present invention can be surveyed by the medical staff distinctly more quickly and easier than displays according to prior art.

According to the present invention, monitoring is based on at least three medically relevant data which usually comprise measurement values obtained by measurement value detection devices or can be derived from such measurement values. A difference is made between data undergoing relatively quick changes, e.g. those of the electrocardiogram, the electro-encephalogram, the arterial pulse curve, the curve of the pressure of the respiratory tract and the like, and data undergoing relatively slow changes, e.g. those of the heart rate, the values of the systolic and diastolic blood pressure, the value of the oxygen saturation, the value of the respiratory rate and the like. In the description hereunder, the above data of the slow-changing type will be referred to as measurement values, and the above data of the fast-changing type are referred to as curves.

At least one of said medically relevant data is a datum which changes relatively quickly, i.e. a curve. Further, this curve must have a periodicity in so far as its basic patterns will be repeated in specific intervals, as is the case, for instance, in the electrocardiogram or the arterial pulse curve per heartbeat or in the curve of the pressure of the respiratory tract per breath.

By means of a display unit associated with the medical system and connected to one or a plurality of measurement value acquisition devices, said at least three medically relevant data are visually represented in a manner generating an apparent three-dimensional optical impression of the display as perceived by the user of the system. Preferably, the representation of said at least three medically relevant data is updated in periodic intervals; these intervals can be derived from those intervals which cause the periodicity of the curve.

If more than three data are to be displayed, the fourth and further dimensions can be represented by further characteristics of the three-dimensionally displayed curve or surface, such as color, various shades of grey, width of lines, brightness and other characteristics.

The above three-dimensional impression is generated by representing said at least three data in an at least three-dimensional coordinate system and by transforming this representation onto a two-dimensional display device according to a predefined arithmetic rule whose parameters can be changed by the user, as well as by use of characteristics suited to enhance the perceived three-dimensional effect, such as surface-effect representation, coloring, apparent illumination etc.

BRIEF DESCRIPTION OF THE DRAWINGS

The invention will be explained in greater detail hereunder with reference to an embodiment illustrated in the accompanying figures.

DETAILED DESCRIPTION OF A PREFERRED EMBODIMENT

In the following description, the invention will be explained—merely by way of example—as applied to spirometry, i.e. the acquisition and visual representation of parameters related to the mechanics of breathing.

For the surveyance of critically ill patients undergoing artificial respiration, the monitoring of parameters of the mechanics of breathing has proven to beneficial from the medical viewpoint. Normally, as a basis for the monitoring of such parameters, the following values are measured the pressure in the breathing circuit and its development over time, the gas flow to and from the patient and its development over time, as well as the volume supplied to the patient and its development over time. The measurement of the gas flow and that of the volume are redundant since the volume is the time integral of the gas flow; frequently, therefore, only the flow is measured and the volume is obtained therefrom by integration over time.

For the measurement of the above values, various methods have found widespread application; one of the most commonly used among these is described in the U.S. Pat. No. 5,111,827 entitled "Respiratory Sampling Device" which is mentioned herein as a reference. According to said patent, a connection piece causing a reduction of the cross-section of the resuscitation tube is inserted into the respirator system. Due to the gas flow through the connection piece, said reduced cross-section causes a pressure difference whose amount is a measure for the flow speed of the gas passing through the tube. This flow speed, as mentioned above, allows for the detection of the volume of the flowing gas. Further, the flow direction can be concluded from the sign of the pressure difference.. The pressure in the breathing circuit is obtained by measuring the pressure prevailing in the connection piece against the atmospheric pressure. Further parameters can be included so as to have the measurement results compensated for physical influence variables, e.g. composition, relative humidity or temperature of the flowing gas. The above mentioned values "pressure" and "flow" are detected by suitable measurement value pick-ups. The output values of these devices can be subjected to a preparatory treatment, if desired, then be digitalized, supplied to one or a plurality of processing devices and be displayed on one or a plurality of display screens. This measuring method is commonly used in medical practice under the name spirometry and is integrated into a number of commercially available patient surveillance monitors as well as respirator and anesthesia apparatus.

Figure 1:
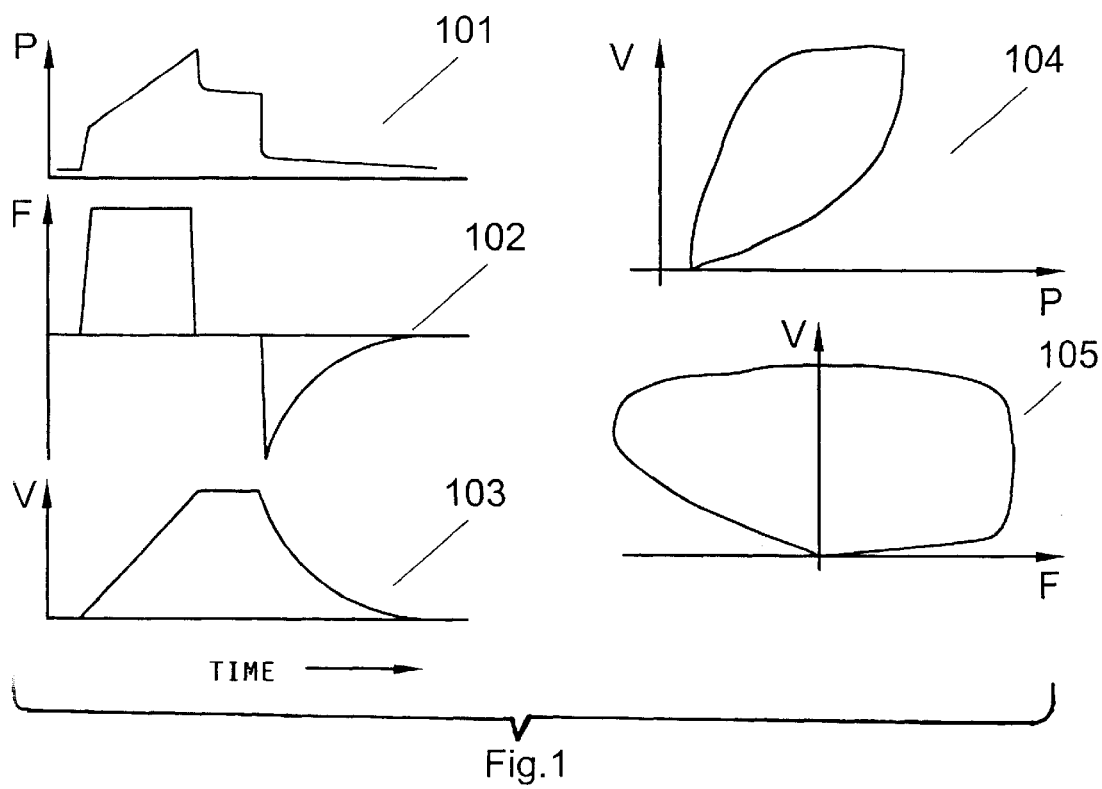
FIG. 1 shows portions of curves for the pressure p of the respiratory tract, flow F and Volume V as well as the loop diagrams V(p) and V(F) in a manner commonly presented by known monitoring systems.

As a form of visual representation on display screens of the above mentioned devices, use is made normally of curves indicating the values "pressure of the respiratory tract" (diagram 101, FIG. 1), referred to hereunder as pressure p, and/or respiratory gas flow (diagram 102, FIG. 1), referred to hereunder as flow F, and/or respiratory volume (diagram 103, FIG. 1), referred to hereunder as volume V. In addition to the representation by means of curves, i.e. the time dependence of the parameters p, F, V, a further form of visual representation has come into use wherein the values of the pressure p and the volume V, as well as the values of the flow F and the volume V are respectively plotted in a two-dimensional coordinate system as dependencies V(p) and V(F) Since the essential characteristics of all of the three curves repeat themselves with each breath, these forms of representation are also called loop diagrams. Also these loop diagrams are shown in FIG. 1 as diagrams 104 and 105.

From specific typical features of these three values, different characteristics related to the mechanics of breathing can now be obtained. Examples of such characteristics of the mechanics of breathing are: respiratory rate, peak pressure, plateau pressure, average pressure, PEEP (Positive End-Expiratory Pressure), respiratory minute volume, inspiratory and expiratory tidal volume, inspiratory and expiratory peak flow, compliance, inspiratory and expiratory resistance, the ratio between inspiration time and expiration time, and so forth. A useful explanation of these and other characteristics of the breathing mechanics and their medical relevance can be found, e.g., in A. Gärtner "Beatmungs- und Narkosetechniken", publ. TÜV Rheinland, which is mentioned herein as a reference. Shown therein are also typical curve shapes of the curves for pressure, flow and volume, and typical loop diagrams. Further explanations on the basic principles of the mechanics of breathing and their derivation are found e.g. in Anaesthesist, Vol. 42, pp. 396–417, "Beatmungsgeräte in der Intensivmedizin", and in Anaesthesist, Vol. 42, pp. 813–832, "Moderne Beatmungsformen; both are therefore mentioned as references.

From the curve shapes 101 to 103 and/or the shapes of the loop diagrams 104, 105, a suitably trained expert will be able—by mere observation of the shape and characteristic features—to gather important recognitions on the condition of a patient and the patient's breathing mechanics. Explained herein as a simple example will be the characteristic feature of a PEEP and the recognition thereof by means of a pressure/volume loop diagram (104). The so-called PEEP (Positive End-Expiratory Pressure) is a phenomenon wherein, at the end of a respiratory cycle, the pressure of the respiratory tract will not in the usual manner return to zero, but, instead—intentionally or unintentionally will have a positive value due to specific manifestations of an illness or specific forms of artificial respiration. In the pressure/volume loop diagram 104 of FIG. 1, this PEEP is clearly visible in that the shown loop is shifted to the right as seen relative to the point of origin of the coordinates. These possibilities made available to a suitably trained medical expert to interpret the curve shapes in the diagrams 101 to 103 and the loops in the diagrams 104, 105 will often obviate the need to observe the exact values of the characteristics of the mechanics of breathing if the rough values of these characteristics can be obtained from the curve shapes 101 to 103 and/or the loop diagrams 104,105 by an extraction of features performed by a suitably skilled user.

Figure 3A:
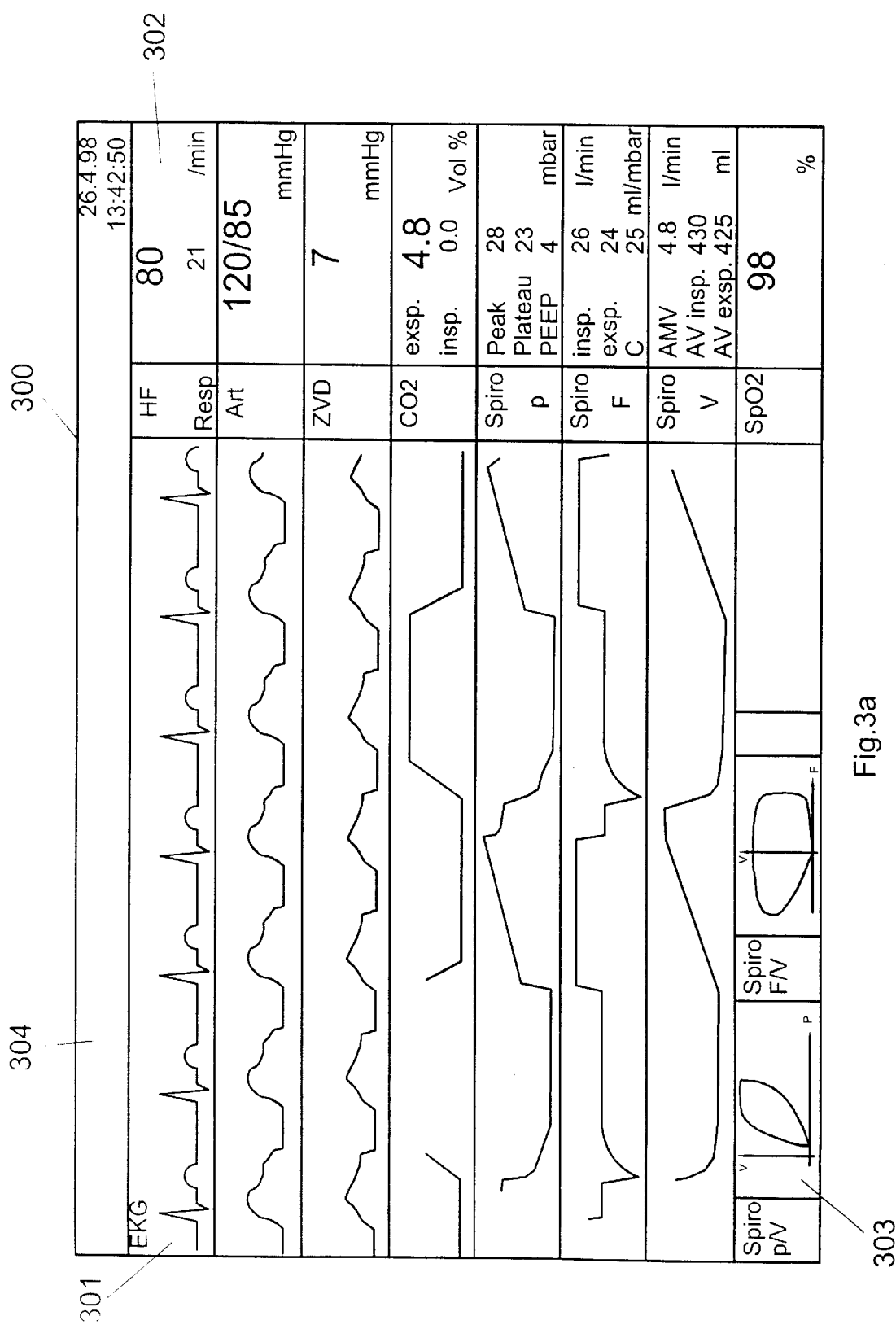
FIG. 3(a) shows an example of the contents of the display screen of a patient surveillance monitor according to the state of the art.

The contents of the display screen 300 of a patient surveillance monitor according to the state of the art, as shown by way of example in FIG. 3a, consists of one or a plurality of display areas for curves 301 and/or of one or a plurality of display areas for measurement values 302 and/or one or a plurality of display areas for graphic representations 303, as well as possible further display areas for further data 304 which can be, e.g., patient identification data.

Depending on the specific type of the patient surveillance monitor to be watched, the respective areas 301 to 304 can be more or less freely placed on the display screen 300 or have a fixed position assigned thereto.

In any case, however, the visual display of the data relevant for the mechanics of breathing will occupy a considerable, not negligible part of the surface area available on the display screen. This leads to a situation where no sufficient area is left anymore for other parameters which are likewise of medical relevance. In practice, this problem is often solved in that a visual representation of some parameters is simply omitted although it would have been beneficial from the medical viewpoint to monitor and display these as well. Another solution would reside in distributing the displayed parameters among several display devices; however, due to the additional costs involved and due to the additional space requirements for further display devices, this solution is adopted only occasionally.

Figure 2:
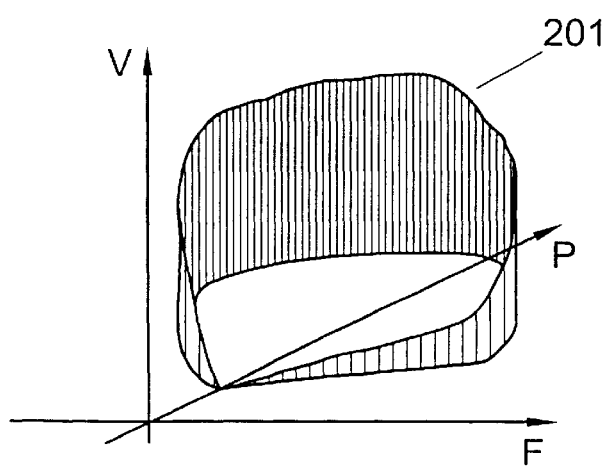
FIG. 2 shows a visual display of the parameters of FIG. 1 in a representation compressed according to the invention.

To accomplish a substantial reduction of the space required to analyze a patient's mechanics of breathing on the display screen of a monitoring device, the instant invention proposes a method to generate a visual representation a in format which is highly compressed as compared to the state of the art. The proposed visual representation is based on a three-dimensional coordinate system as shown in FIG. 2, which according to the preferred embodiment is a Cartesian coordinate system but can also be a coordinate system of cylindrical, spherical or a different desired shape. Now, as shown in FIG. 2, based on an exemplary assignment of the three spatial axes x (horizontal), y (rearward) and z (vertical) to the values flow F, pressure p and volume V, each point which before was displayed on a display screen according to the conventional representation of curves, is here represented as a point in a three-dimensional flow-pressure-volume space.

To enhance the three-dimensional impression of the figure 201 generated by this plurality of points, a connecting line is drawn from each point of this plurality of points to the respective next point of the plurality of points. To achieve a still further enhancement of the three-dimensional impression of the figure 201, a vertical connecting line can be drawn from each point of this plurality of points to points having the same coordinate data for flow-and pressure as the point of origin of this line, but a value for a volume of zero.

According to an exemplary embodiment of the invention, said figure 201 in the flow-pressure-volume space is generated after each completed breath and is represented on a display device of the patient surveillance monitor. In the process, the three-dimensional flow-pressure-volume space is transformed into the two-dimensional x-y-surface -of the display device in that points situated in the background are covered by points situated in the foreground.

According to the instant exemplary embodiment, the flow axis extends in the horizontal direction, the volume axis extends in the vertical direction and the pressure axis extends in the rearward direction; in FIG. 2, this configuration is illustrated through an angle of 30° between the pressure and flow axes. Further, a different coloring is given to the inner and outer surfaces of the annular figure 201 which is being generated. The colors can be made selectable by the user.

According to a further aspect of the present invention, the rate of change of the parameters "flow" and/or "pressure" can be read on the basis of the line density of the above mentioned vertical connecting lines, with a small line density indicating a high rate of change and a large line density indicating a low rate of change, since the acquisition of the measurement values for the parameters p, F, V is normally performed by scanning in equidistant time intervals.

According to a further aspect of the present invention, also a number of values larger than three can be plotted in a representation with three or more dimensions; the fourth value and further values will then be visually represented by changes of the attributes of a three-dimensional figure., e.g. color, grey shade, width of lines, line density, brightness and the like.

According to a further aspect of the present invention, the scaling, i.e. the relation of the pure parameter value to the x-y coordinate of a display device, of the flow and/or pressure and/or volume axes, can be set by the user and can be caused to adapt itself to the value of the individual parameters so that the resulting figures can be completely displayed on the display area available in the display device.

According to a further aspect of the present invention, a possibility is provided for visual representation—in addition to that of a first figure (201) corresponding to the respective breath of a patient —of a second figure, preferably in different colors, within or outside said flow-pressure-volume coordinate system of the first figure 201, thus allowing the user to perform a. simple visual comparison of the displayed first and second figures. Said second figure can have been generated by storing the data of a first figure at an earlier point of time.

According to a further aspect of the present invention, the parameters of the arithmetic rule used for the transformation of the flow-pressure-volume space into the two-dimensional x-y-surface of a display device can be changed at random by the user so that the nature of the visual display of the resultant figure 201 can be varied as desired. For instance, the displayed figure according to FIG. 2 can be turned, tilted or inclined as well as be enlarged, reduced or distorted.

For the compressed representation of data from spirometry as provided in the present example of a possible application of the invention, the above described assignment of the three spatial axes appears useful because the resultant figures are easily interpretable. The representation of the volume along the vertical line is in analogy with the notion in medical practice that present respiration or anaesthesia devices comprise an elastic bellows arranged to move up and down to supply a volume to the patient. The representation of the flow along the horizontal line appears favorable because the flow will change its sign in the course of a respiratory cycle and thus will generate figures with left-right-symmetry. The representation of the pressure in the rearward direction enhances the spatial impression of the resultant figures because, in the course of a respiratory cycle, the pressure will normally increase from a value near zero to a peak pressure and then will drop again to a value near the original pressure.

Apart from the reduced space requirements in a display device due to the compressed visual representation, the method of the compressed representation according to the invention offers the further advantage that this visual representation can be quickly surveyed and easily interpreted by suitably trained medical staff. An example would reside in the detection of a typical feature of a PEEP, as already described further above, by means of the visual representation according to the invention. As shown by way of example in FIG. 2, the figure 201 generated from the individual measurement values has been noticeably shifted to the rear relative to the plane defined by the flow and volume axes. In a manner similar to that of the PEEP application, also other characteristics of the mechanics of breathing can be visually extracted by a medical expert of relevant skills. This extraction of features—performed by suitably trained medical staff—from forms of visual representation which would have only little significance to non-experts in medical science, is common medical practice in various fields, such as sonography, radiology or cardiology.

Figure 3B:
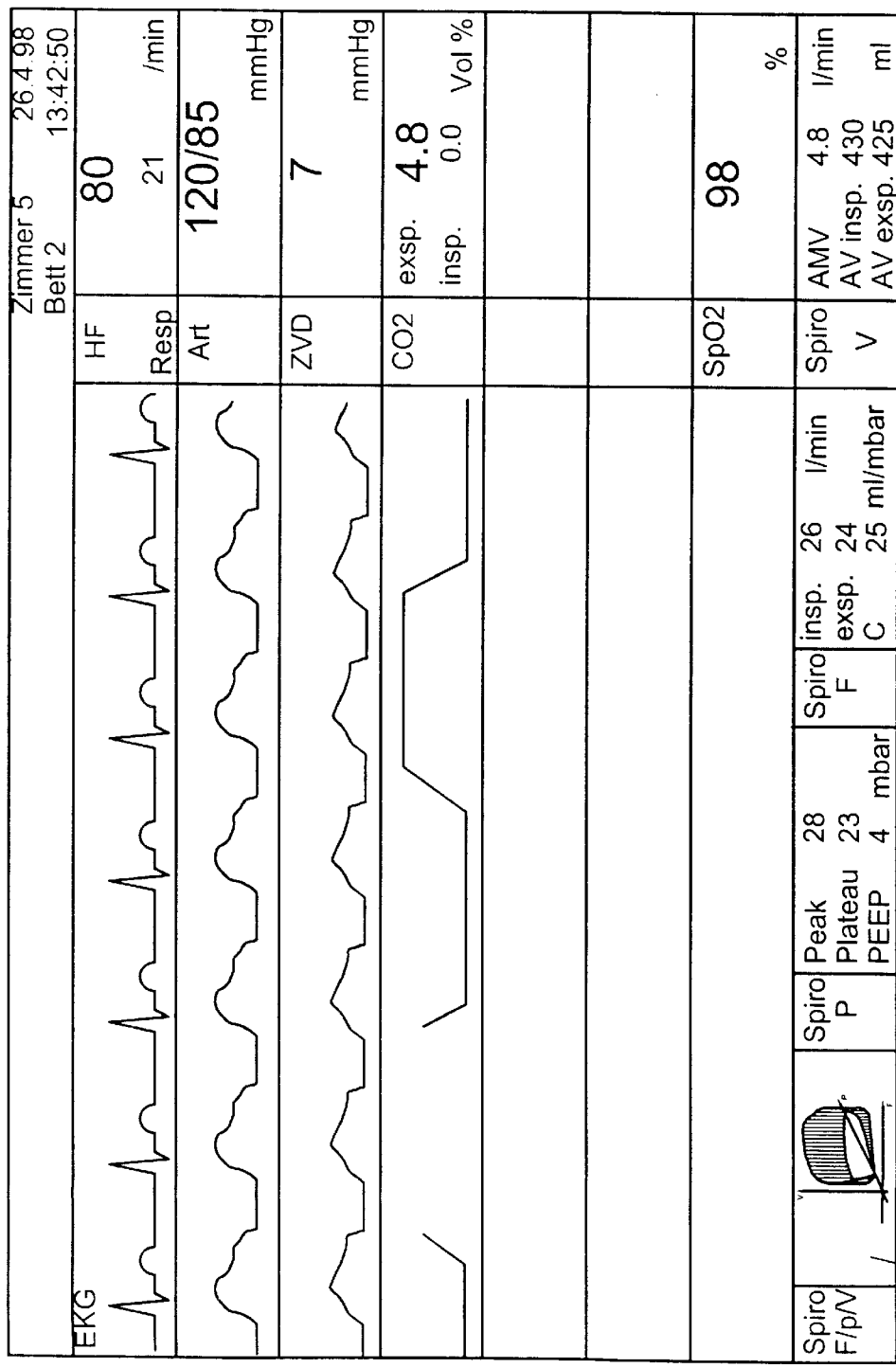
FIG. 3(b) shows an example of the contents of the display screen of a patient surveillance monitor according to the invention wherein the data of FIG. 3a are displayed as compressed according to the invention.

FIG. 3b shows the content of the display screen of the patient surveillance monitor of FIG. 3a as generated by use of the instant method for compressed visual representation of medical data. It is obvious that the application of the method of the invention provides for a considerable space saving in a display device when compared to the conventional visual representation according to FIG. 3a. The thus saved space can be utilized for other parameters, for a more easily surveyed structural layout of the display area, for a reduction of the size of the display device or for a combination of these possibilities. The three-dimensional figure 305 shown in FIG. 3b can be understood as a graphic representation which, depending on the respective basic concept of the patient surveillance monitor, can be more or less freely placed within the display area or have a fixed position assigned thereto. The three-dimensional figure 305 can be displayed on a display screen in addition to the conventional representation or instead of the latter. According to the principles of the instant invention, exclusively these three-dimensional figures, optionally along with the numerical representation of the above mentioned breathing characteristics, should be displayed for an evaluation of the mechanics of breathing, provided that the specialized medical staff has been suitably trained. This represents an essential step towards a reduction of the initially mentioned "mental overload".

It will be evident that the instant method for the compressed visual representation of medical data is not restricted to the above example of a representation of data relevant for the mechanics of breathing but is suitably applicable to a large variety of medical data. To fulfill the purpose of the invention, it is also not necessarily required to use exclusively said relatively fast-changing data, i.e. curves according to the above definition; instead, relatively fast-changing data can be visually represented in a compressed format together with relatively slow-changing data according to the described method. Thus, for instance, a curve indicating the carbon dioxide concentration of the respiratory gas of a patient can be compressed together with the curves of the patient's respiratory tract and arterial oxygen saturation. Upon closer consideration, it will be understood that the above described method is suited for a wide range of applications in the field of medicine.

What is claimed is:

1. A method of displaying a simultaneous compressed visual representation of medically relevant parameters comprising the steps of:

(a) acquiring data of at least three disparate medically relevant parameters in which at least one of the three disparate medically relevant parameters defines a periodical curve over time, (b) establishing a three-dimensional coordinate system defined by at least three angularly related axes, (c) combining the acquired disparate data into a three-dimensional data volume substantially representative of the disparate data, (d) transforming the three-dimensional data volume into a substantially equivalent two-dimensional data representation, and (e) displaying the two-dimensional representation relative to the three-dimensional coordinate system including the at least three angularly related axes thereof thereby obtaining a simultaneous compressed visual representation of the at least three disparate medically relevant parameters.

2. The method as defined in claim 1 including the step of updating at least one of the parameters incident to performing step (e).

3. The method as defined in claim 1 including the step of updating at least one of the parameters incident to performing step (e) in time intervals corresponding to one period of the at least one relevant parameter.

4. The method as defined in claim 1 including the step of periodically updating at least one of the parameters incident to performing step (e).

5. The method as defined in claim 1 including the step of updating at least one of the parameters incident to performing step (e) in time intervals corresponding to one period of the at least one relevent parameter, and the point in time for performing the updating being dependent upon any one of the three parameters.

6. The method as defined in claim 1 including the step of updating at least one of the parameters incident to performing step (e) in time intervals corresponding to one period of the at least one relevant parameter, and the point in time for performing the updating being time-dependent.

7. The method as defined in claim 1 including the steps of (f) establishing a fourth relevant parameter, and (g) performing step (e) by additionally displaying the fourth parameter as part of the displayed two-dimensional representation.

8. The method as defined in claim 1 including the steps of (f) establishing time as a fourth relevant parameter, and (g) performing step (e) by additionally displaying the fourth parameter as part of the displayed two-dimensional representation.

9. The method as defined in claim 1 wherein the at least one medically relevant parameter is selected from the group comprising the pressure of the respiratory tract (p(t)), respiratory gas flow (F(t)) and respiratory gas volume (V(t)).

10. The method as defined in claim 1 wherein the coordinate system established by the performance of step (b) is one of a Cartesian, cylindrical and spherical coordinate system.

11. The method as defined in claim 1 including performing step (c) by combining numerous disparate data as data points representative of the three-dimensional data volume, and enhancing the displayed two-dimensional representation of step (e) by drawing connecting lines from data points of the two-dimensional representation to corresponding points representing a projection of the two-dimensional representation.

12. The method as defined in claim 1 including the steps of enhancing the displayed two-dimensional representation of step (e) by one of (i) coloring at least one selected surface portion of the two-dimensional representation, (ii) shading at least one selected surface portion of the two-dimensional representation, (iii) lining at least one selected surface portion of the two-dimensional representation utilizing lines of different widths, (iv) lining at least one selected surface portion of the two-dimensional representation utilizing different line densities, and (v) variably brightening at least one selected surface portion of the two-dimensional representation.

13. The method as defined in claim 10 including the steps of enhancing the displayed two-dimensional representation of step (e) by one of (i) coloring at least one selected surface portion of the two-dimensional representation, (ii) shading at least one selected surface portion of the two-dimensional representation, (iii) lining at least one selected surface portion of the two-dimensional representation with lines of different widths, (iv) lining at least one selected surface portion of the two-dimensional representation utilizing different line densities, and (v) variably brightening at least one selected surface portion of the two-dimensional representation.

14. The method as defined in claim 6 including the step of representing the fourth parameter as part if the displayed two-dimensional representation by at least one feature selected from the group comprising color, shade, gray tone, line width, line density and brightness.

15. The method as defined in claim 6 including the step of representing the fourth parameter as part of the displayed two-dimensional representation by at least one feature selected from the group comprising color, shade, gray tone, line width, line density and brightness, the fourth parameter is time, and time influences the at least one selected feature.

16. The method as defined in claim 1 where in step (e) is performed at current time by current time data acquired by the performance of step (a), and performing the step of displaying at least one further display other than that displayed by the performance of step (e).

\* \* \* \* \*